(12) United States Patent
Lentz et al.

(10) Patent No.: US 7,901,367 B2
(45) Date of Patent: Mar. 8, 2011

(54) WIRE GUIDE ADVANCEMENT SYSTEM

(75) Inventors: David Christian Lentz, Bloomington, IN (US); Jeffry S. Melsheimer, Springville, IN (US)

(73) Assignee: Cook Incorporated, Bloomington, IL (US)

(*) Notice: Subject to any disclaimer, the term of this patent is extended or adjusted under 35 U.S.C. 154(b) by 48 days.

(21) Appl. No.: 11/475,509

(22) Filed: Jun. 27, 2006

(65) Prior Publication Data

US 2007/0010763 A1 Jan. 11, 2007

Related U.S. Application Data

(60) Provisional application No. 60/695,495, filed on Jun. 30, 2005.

(51) Int. Cl.
*A61M 25/00* (2006.01)
(52) U.S. Cl. .......................................... 600/585
(58) Field of Classification Search .............. 600/585, 600/424; 606/164.01, 164.13, 180
See application file for complete search history.

(56) References Cited

U.S. PATENT DOCUMENTS

| | | | |
|---|---|---|---|
| 3,521,620 A | 7/1970 | Cook | |
| 3,547,103 A | 12/1970 | Cook | |
| 3,890,977 A | 6/1975 | Wilson | |
| 4,406,656 A * | 9/1983 | Hattler et al. | 604/523 |
| 4,548,206 A | 10/1985 | Osborne | |
| 4,650,472 A | 3/1987 | Bates | |
| 4,665,906 A | 5/1987 | Jervis | |
| 4,824,435 A | 4/1989 | Giesy et al. | |
| 4,925,445 A * | 5/1990 | Sakamoto et al. | 604/528 |
| 4,934,380 A | 6/1990 | De Toledo | |
| 4,984,581 A | 1/1991 | Stice | |
| 5,069,226 A | 12/1991 | Yamauchi et al. | |
| 5,129,890 A | 7/1992 | Bates et al. | |
| 5,131,407 A * | 7/1992 | Ischinger et al. | 600/585 |
| 5,159,861 A | 11/1992 | Anderson | |
| 5,213,111 A | 5/1993 | Cook et al. | |
| 5,242,759 A | 9/1993 | Hall | |
| 5,243,996 A | 9/1993 | Hall | |
| 5,251,640 A | 10/1993 | Osborne | |
| 5,263,964 A * | 11/1993 | Purdy | 606/200 |

(Continued)

FOREIGN PATENT DOCUMENTS

EP 0 436 303 A1 11/1990

(Continued)

OTHER PUBLICATIONS

Wang et al. "Technical and Prognostic Outcomes of Double-Balloon Pericardiotomy for Large malignancy-Related Pericardial Effusions," Chest 112 Sep. 3, 2002.*

(Continued)

*Primary Examiner* — Max Hindenburg
*Assistant Examiner* — Michael C Stout
(74) *Attorney, Agent, or Firm* — Brinks Hofer Gilson & Lione

(57) ABSTRACT

The medical device includes a secondary wire guide and an advancement device. The advancement device has a tubular portion with a distal opening and a proximal opening. An edge region of the tubular portion forms the distal opening. A primary wire guide extends through the tubular portion. The secondary wire guide also extends into the tubular portion and has a distal portion configured to engage the edge region of the tubular portion. Accordingly, the secondary wire guide is advanced as the advancement device is translated into the blood vessel.

12 Claims, 4 Drawing Sheets

U.S. PATENT DOCUMENTS

| | | | |
|---|---|---|---|
| 5,267,958 | A | 12/1993 | Buchbinder et al. |
| 5,306,261 | A | 4/1994 | Alliger et al. |
| 5,325,746 | A | 7/1994 | Anderson |
| 5,328,480 | A | 7/1994 | Melker et al. |
| 5,354,257 | A | 10/1994 | Roubin et al. |
| 5,402,799 | A | 4/1995 | Colon et al. |
| 5,488,959 | A | 2/1996 | Ales |
| 5,597,378 | A | 1/1997 | Jervis |
| 5,718,692 | A * | 2/1998 | Schon et al. ............... 604/264 |
| 5,776,079 | A | 7/1998 | Cope et al. |
| 5,925,059 | A * | 7/1999 | Palermo et al. ............. 606/191 |
| 5,993,424 | A | 11/1999 | Lorenzo et al. |
| 5,997,526 | A | 12/1999 | Giba et al. |
| 6,139,510 | A | 10/2000 | Palermo |
| 6,217,567 | B1 | 4/2001 | Zadno-Azizi et al. |
| 6,245,076 | B1 * | 6/2001 | Yan ............................. 606/108 |
| 6,254,550 | B1 | 7/2001 | McNamara et al. |
| 6,254,610 | B1 * | 7/2001 | Darvish et al. .............. 606/108 |
| 6,306,141 | B1 | 10/2001 | Jervis |
| 6,348,041 | B1 | 2/2002 | Klint |
| 6,383,146 | B1 | 5/2002 | Klint |
| 6,482,169 | B1 * | 11/2002 | Kuhle ......................... 604/6.16 |
| 6,500,130 | B2 | 12/2002 | Kinsella et al. |
| 6,502,606 | B2 | 1/2003 | Klint |
| 6,544,197 | B2 * | 4/2003 | DeMello ...................... 600/585 |
| 6,605,049 | B1 * | 8/2003 | Wagner et al. ............... 600/585 |
| 6,613,002 | B1 | 9/2003 | Clark et al. |
| 6,638,372 | B1 | 10/2003 | Abrams et al. |
| 6,682,608 | B2 | 1/2004 | Abrams et al. |
| 6,805,676 | B2 | 10/2004 | Klint |
| 6,840,451 | B2 * | 1/2005 | Allen ...................... 235/462.09 |
| 6,922,579 | B2 * | 7/2005 | Taimisto et al. ............. 600/374 |
| 7,037,293 | B2 * | 5/2006 | Carrillo et al. ........... 604/164.13 |
| 2001/0004699 | A1 | 6/2001 | Gittings et al. .............. 606/153 |
| 2002/0082524 | A1 * | 6/2002 | Anderson et al. ............. 600/585 |
| 2003/0097095 | A1 * | 5/2003 | Brady et al. ............. 604/164.13 |
| 2003/0144670 | A1 * | 7/2003 | Pavcnik et al. .............. 606/108 |
| 2003/0225435 | A1 * | 12/2003 | Huter et al. .................... 606/200 |
| 2003/0233117 | A1 * | 12/2003 | Adams et al. ................. 606/200 |
| 2004/0006365 | A1 * | 1/2004 | Brady et al. .................. 606/200 |
| 2004/0039304 | A1 * | 2/2004 | Connors et al. .............. 600/585 |
| 2004/0215208 | A1 | 10/2004 | Foushee et al. |
| 2004/0220473 | A1 * | 11/2004 | Lualdi .......................... 600/435 |
| 2004/0225175 | A1 * | 11/2004 | Moody et al. .................... 600/3 |
| 2005/0059890 | A1 * | 3/2005 | Deal et al. .................... 600/433 |
| 2005/0222580 | A1 * | 10/2005 | Gifford et al. ................ 606/108 |
| 2006/0030864 | A1 * | 2/2006 | Kennedy et al. ............. 606/108 |
| 2006/0100544 | A1 | 5/2006 | Ayala et al. |
| 2006/0100545 | A1 | 5/2006 | Ayala et al. |

FOREIGN PATENT DOCUMENTS

| | | |
|---|---|---|
| WO | WO 99/44510 | 9/1999 |
| WO | WO 00/74565 A1 | 12/2000 |
| WO | WO 02 094364 A2 | 11/2002 |
| WO | WO 2004/049970 A2 | 6/2004 |
| WO | WO 2005/011788 A1 | 2/2005 |
| WO | WO 2005/025660 A1 | 3/2005 |
| WO | WO 2005/089852 A1 | 9/2005 |

OTHER PUBLICATIONS

Wang et al. "Technical and Prognostic Outcomes of Double-Balloon Pericardiotomy for Large malignancy-Related Pericardial Effusions," Chest 112 Sep. 3, 2002.*

Wang et al. "Technical and Prognostic Outcomes of Double-Balloon Pericardiotomy for Large malignancy-Related Pericardial Effusions," Chest 112 Sep. 3, 2002.*

The Journal of Invasive Cardiology entitled "Use of a Second Buddy Wire During Percutaneous Coronary Interventions: A Simple Solution for Some Challenging Situations" dated Apr. 25, 2005, pp. 1-8.

* cited by examiner

WIRE GUIDE ADVANCEMENT SYSTEM

PRIORITY CLAIM

This application claims the benefit of U.S. provisional application 60/695,495, filed Jun. 30, 2005.

BACKGROUND

1. Field of the Invention

The present invention generally relates to a medical device and method for deploying multiple wire guides percutaneously into a blood vessel.

2. Description of Related Art

The Seldinger technique has been used successfully for many years to introduce wire guides percutaneously into a blood or other vessel of humans and animals. The technique is popular because minimal trauma is introduced to the surrounding tissue. According to the technique, a needle is introduced into a vessel. A straightened wire guide is inserted into the vessel through the needle. After the wire guide is advanced into the vessel, the needle may be removed over the wire guide and the wire guide secured to limit further advancement into the vessel. Subsequently, a dilator may be advanced over the wire into the insertion point to open up the site and facilitate introduction of other medical devices, such as catheters. Two wire guides may be implemented adjacent to each other in some procedures. In such instances, the secondary wire guide is typically introduced after the first and then advanced to the same destination. Each wire guide may have different characteristics and is advanced separately through the vasculature to the region of interest. For example, the secondary wire guide may be stiffer than the first. Individually advancing each wire guide through tortuous vessels can be time consuming and introduce additional trauma to the vessel.

In view of the above, it is apparent that there exists a need for a medical device and improved method for sequentially deploying multiple wire guides in adjacent relationship.

SUMMARY

In satisfying the above need, as well as overcoming the enumerated drawbacks and other limitations of the related art, the present invention provides a medical device and improved method for deploying multiple wire guides.

The medical device includes a secondary wire guide and an advancement device. The advancement device has a tubular portion with a distal opening and a proximal opening. An edge region of the tubular portion forms the distal opening. A primary wire guide extends through the tubular portion. The secondary wire guide also extends into the tubular portion and has a distal portion configured to engage the edge region of the tubular portion. Accordingly, the secondary wire guide is advanced as the advancement device is translated into the blood vessel.

In another aspect of the present invention, the distal portion of the guide tubular body engages the tip of the secondary wire guide. In addition, a width of the distal portion is greater than a width of the distal opening less the diameter of the primary wire guide. Alternatively, the width of the distal portion may be simply greater than the width of the distal opening.

In another aspect of the present invention, the advancement device includes a handle portion that extends proximally from the tubular portion. Further, the handle portion of the advancement device has a unique marker with respect to the primary wire guide and the secondary wire guide. Further, the unique marker may include a color absent from the primary and secondary wire guide, or the unique marker may be a tactile marker.

In another aspect of the present invention, the secondary wire guide may be attached to the advancement device through a melt bond or adhesive.

Further objects, features and advantages of this invention will become readily apparent to persons skilled in the art after a review of the following description, with reference to the drawings and claims that are appended to and form a part of this specification.

DETAILED DESCRIPTION

Figure 1:
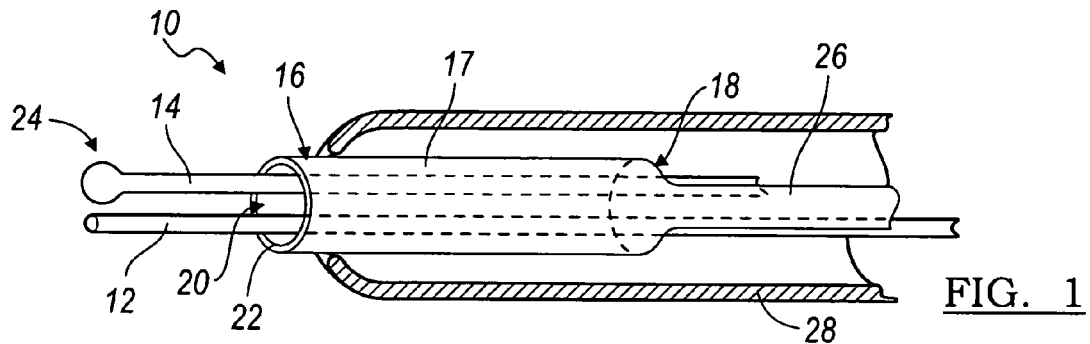
FIG. 1 is a sectional side view of a medical device in accordance with one embodiment of the present invention.
Figure 2:
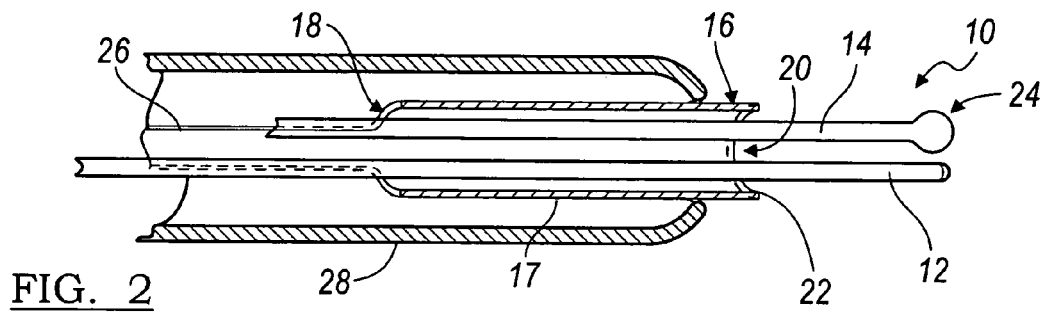
FIG. 2 is another sectional side view of the medical device in FIG. 1.

Referring now to FIGS. 1 and 2, a medical device embodying the principles of the present invention is illustrated therein and designated at 10. The medical device 10 includes a primary wire guide 12, a secondary wire guide 14, and an advancement device 16. The primary wire guide 12 and secondary wire guide 14 may have the same or different diameters, and may have the same or different stiffnesses. Accordingly, the secondary wire guide 14 may be more stiff than the primary wire guide 12 or the primary wire guide 12 may be more stiff than the secondary wire guide 14.

In the embodiment shown, the primary wire guide 12 is generally quite flexible and is introduced percutaneously into a blood or other vessel, for example a biliary tract, urinary tract, gastrointestinal tract, airway, etc. The primary wire guide 12 extends through the advancement device 16. The secondary wire guide 14 also extends through the advancement device 16 and generally is advanced to the same region of interest as the primary wire guide 12. The advancement device 16 has a tubular portion 17. The tubular portion 17 includes a proximal opening 18 and a distal opening 20. An edge portion 22 of the advancement device 16 forms the distal opening 20. The secondary wire guide 14 extends into the distal opening 20 through the tubular portion 17 and out of the proximal opening 18. A distal portion 24, shown as the tip of the secondary wire guide 14, is configured to engage the edge portion 22 of the advancement device 16. To aid during advancement of the secondary wire guide 14, the distal portion 24 may be made of a radiopaque material, or the tubular portion 17 may be made of a radiopaque material, or the edge portion 22 may be made of a radiopaque material, or any combination of these. Accordingly, as the advancement device 16 is advanced over the primary wire guide 12, the distal portion 24 will engage the advancement device 16 thereby advancing the secondary wire guide 14 therewith. Further, a guiding catheter 28 may be provided to facilitate translation of the advancement device 16 which reduces trauma to the blood or other vessel 30. To facilitate manipulation of the advancement device 16, a handle portion 26 extends from the tubular portion 17 and is accessible external the blood or other vessel 30 to allow manipulation by the clinician.

Figure 3:
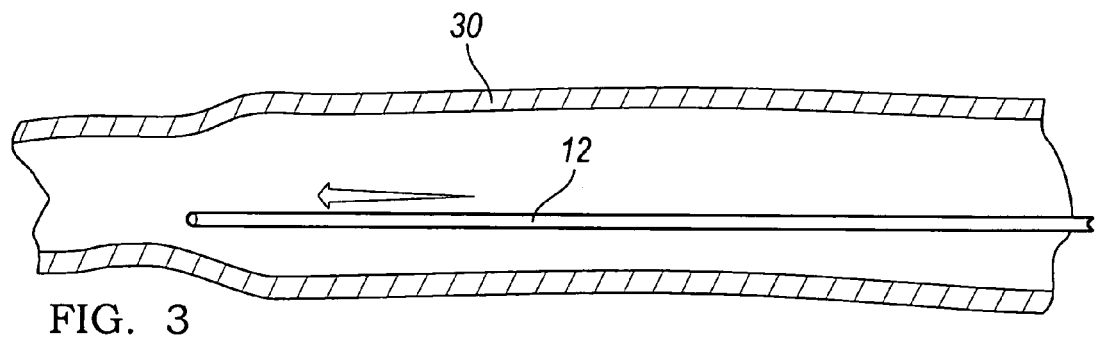
FIG. 3 is a sectional view of a blood vessel illustrating an inserted primary wire guide in accordance with the present invention.

Now referring to FIGS. 3 through 8, a method for deploying multiple wire guides, in accordance with the present invention, is provided. The primary wire guide 12 is percutaneously introduced into the blood or other vessel 30 and advanced to a region of interest, as shown in FIG. 3.

Figure 4:
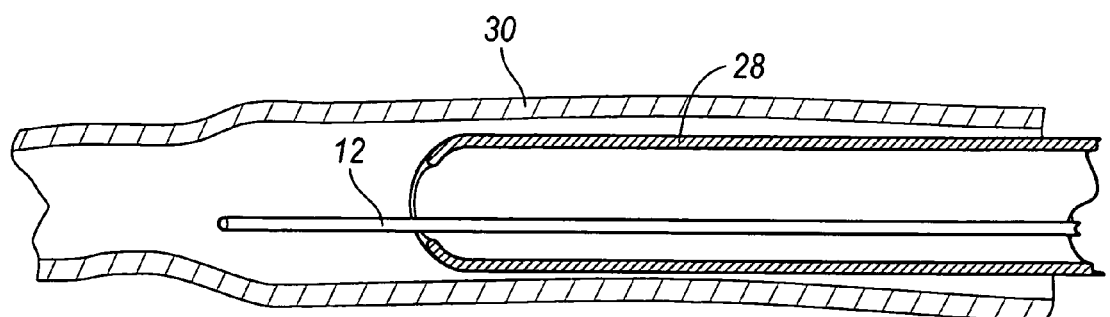
FIG. 4 is a sectional view of a blood vessel showing the guiding catheter inserted over the primary guide wire.
Figure 5:
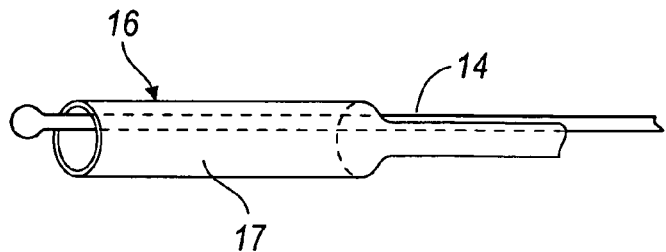
FIG. 5 is a side view of the secondary wire guide and the advancement device in accordance with the present invention.
Figure 6:
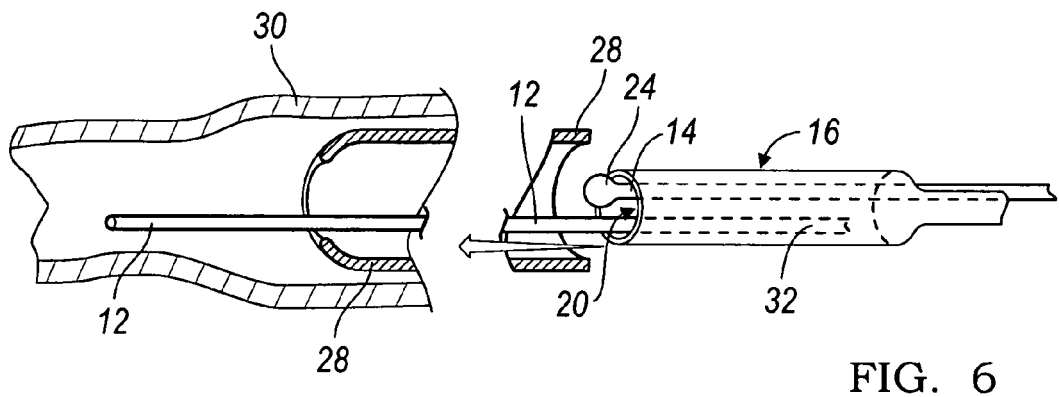
FIG. 6 is a side view of the advancement device being inserted over the primary wire guide in accordance with the present invention.

Now referring to FIG. 4, the guiding catheter 28 may be percutaneously introduced into the blood or other vessel 30 over the primary wire guide 12 and advanced through the blood or other vessel 30 until the tortuosity or vessel dimensions restrict further advancement. As shown in FIG. 5, the advancement device 16 is advanced over the proximal end of the secondary wire guide 14, so that the secondary wire guide 14 extends through the distal opening 20 and the proximal opening 18 of the tubular portion 17. Now referring to FIG. 6, the advancement device 16 containing the secondary wire guide 14 is advanced over the proximal end 32 of the primary wire guide 12. As the advancement device 16 is advanced over the primary wire guide 12, the distal portion 24 of the secondary wire guide 14 engages the advancement device 16 thereby advancing the secondary wire guide 14 and the advancement device 16 simultaneously. The secondary wire guide 14 is introduced adjacent to the primary wire guide 12, while the advancement device 16 is percutaneously introduced into the blood or other vessel 30 over the primary wire guide 12.

Figure 7:
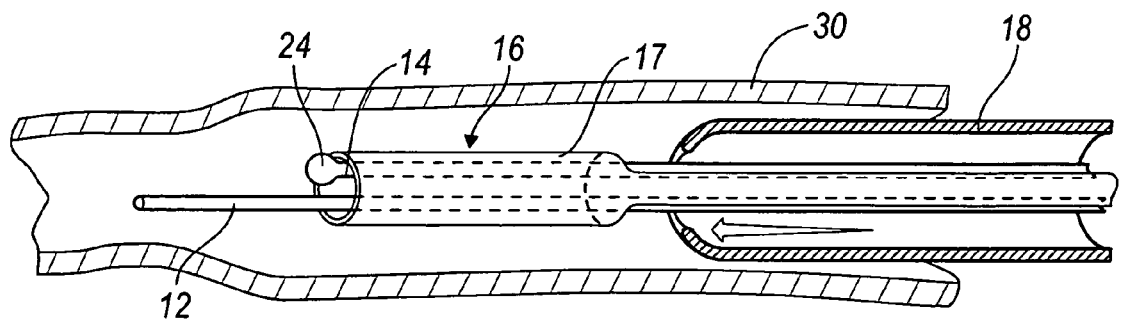
FIG. 7 is a cutaway side view of the blood vessel illustrating the advancement of the secondary wire guide through the guide catheter and over the primary wire guide in accordance with the present invention.

Referring now to FIG. 7, the advancement device 16 is inserted into the blood or other vessel 30 through the guiding catheter 28 along the primary wire guide 12. The distal portion 24 of the secondary wire guide 14 continues to engage the advancement device 16 as the tubular portion 17 of the advancement device 16 is advanced distal the guiding catheter 28.

Figure 8:
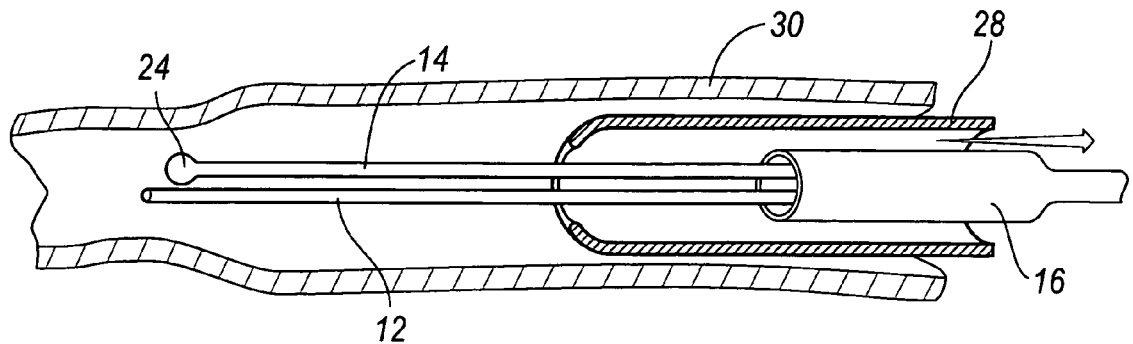
FIG. 8 is a sectional side view of the blood vessel showing removal of the advancement device in accordance with the present invention.

Referring now to FIG. 8, when the secondary wire guide 14 has been advanced to the region of interest along the first wire guide 12, the advancement device 16 may be retracted over the primary wire guide 12. Accordingly, the retraction of the advancement device 16 disengages the distal portion 24 of the secondary wire guide 14 from the advancement device 16.

Figure 9:
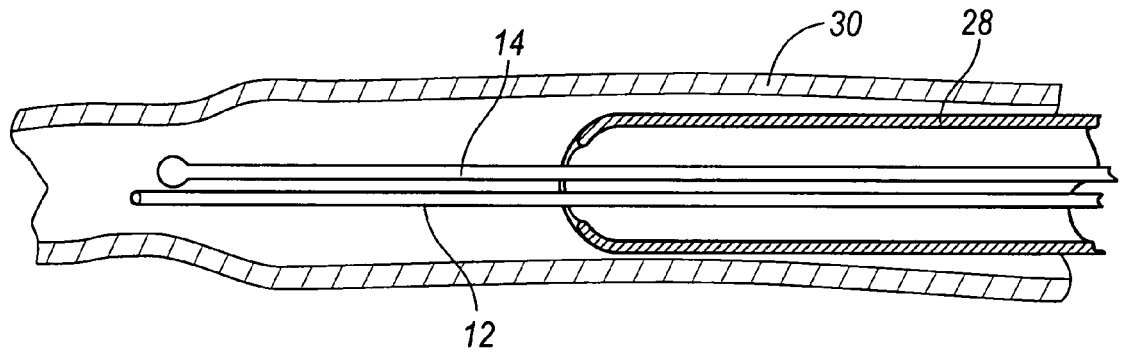
FIG. 9 is a sectional side view of the blood vessel showing the fully deployed primary and secondary wire guide in accordance with the present invention.

As shown in FIG. 9, the advancement device 16 is fully removed from the primary wire guide 12 and the secondary wire guide 14, allowing other devices to be advanced separately over either one or both of the primary wire guide 12 and the secondary wire guide 14 to treat the region of interest within the blood or other vessel 30.

Figure 10:
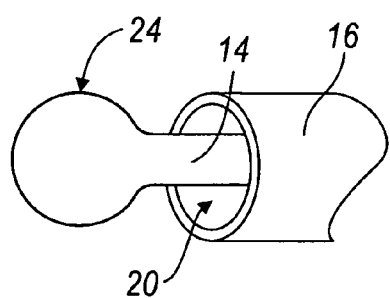
FIG. 10 shows the distal tip of the secondary wire guide where the distal tip is larger than the diameter of the distal opening.

To facilitate engagement of the distal portion 24 of the secondary wire guide 14 with the advancement device 16, the distal portion 24 may have a width greater than the width of the distal opening 20 of the advancement device 16 as shown in FIG. 10. Alternatively, as shown in previous figures, the distal portion 24 may have a width greater than the width of the distal opening 20 less the diameter of the primary wire guide 12.

Figure 11:
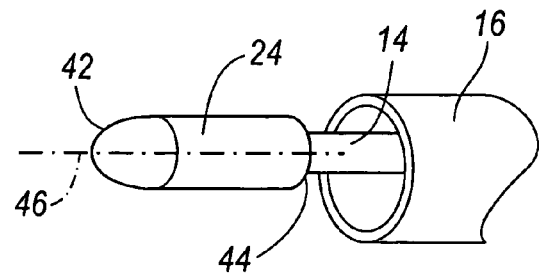
FIG. 11 shows the distal tip of the secondary wire guide where the tip is generally cylindrically shaped.

Now referring to FIG. 11, the distal portion 24 of the secondary wire guide 14 may have a distal surface 42 that has a generally conical or more specifically a generally paraboloid shape. In addition, the proximal surface 44 may have a surface angle that is substantially perpendicular to a central axis 46 of the secondary wire guide 14. Accordingly, the distal surface 42 provides improved advancement of the secondary wire guide 14 while the proximal surface 44 provides improved engagement with the advancement device 16.

Figure 12:
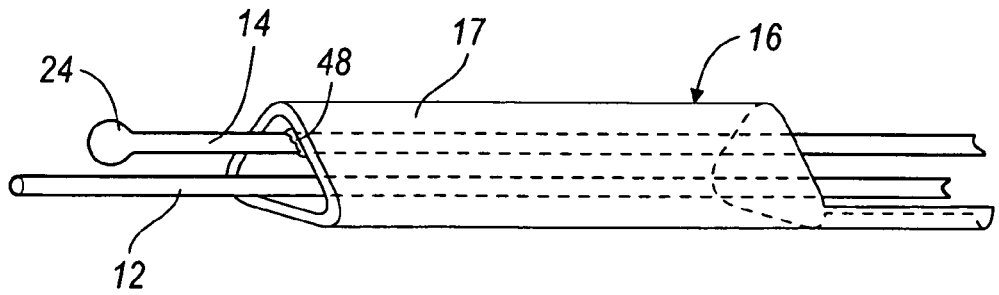
FIG. 12 is a side view of the advancement device where the advancement device has a tubular section with a generally polygonal cross section.

Now referring to FIG. 12, in another embodiment of the present invention, the tubular portion 17 of the advancement device 16 may have a generally polygonal cross-sectional area, shown as a triangular cross-sectional area. The triangular cross-sectional area may be used to increase the stiffness of the advancement device 16 and in certain instances may also improve the engagement between the distal portion 24 of the secondary wire guide 14 and the edge portion 22 of the advancement device 16. Other cross-sectional shapes may be implemented, including various polygonal and elliptical shapes.

Also shown in FIG. 12, the secondary wire guide 14 may be attached to the advancement device 16. The attachment may be through a bond 48, such as an adhesive or melt bonding of the secondary wire guide with the advancement device 16. As such, the secondary wire guide 14 would be engaged with the advancement device 16 thereby simultaneously advancing the secondary wire guide 14 and the advancement device 16 over the primary wire guide 12. However, when the secondary wire guide 14 has reached the region of interest, the bond 48 may be removed by introduction of a dissolving agent, through a current sent through the secondary wire guide to cause a chemical or thermal reaction, or mechanically, for example, by rotating the secondary wire guide 14 to sever the bond 48. The secondary wire guide 14 may be threaded into the advancement device 16 and disengaged therefrom by rotating the secondary wire guide 14 relative to the advancement device 16.

Figure 13:
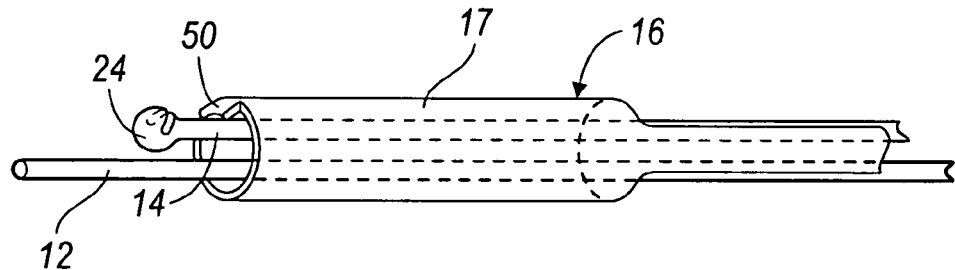
FIG. 13 is a side view of the advancement device including a tab for engaging the distal portion of the secondary wire guide.

Alternatively, in another embodiment shown in FIG. 13, the secondary wire guide 14 may be provided in a mechanical locking engagement with the advancement device 16. For example, a tab 50 may extend from a tubular portion 17 of the advancement device 16. The distal portion 24 of the wire guide 14 may be configured to lockingly engage the tab 50 in the distal and proximal direction. However, by rotating the secondary wire guide 14 the distal portion 24 may be disengaged from the tab 50 allowing removal of the advancement device 16.

Figure 14:
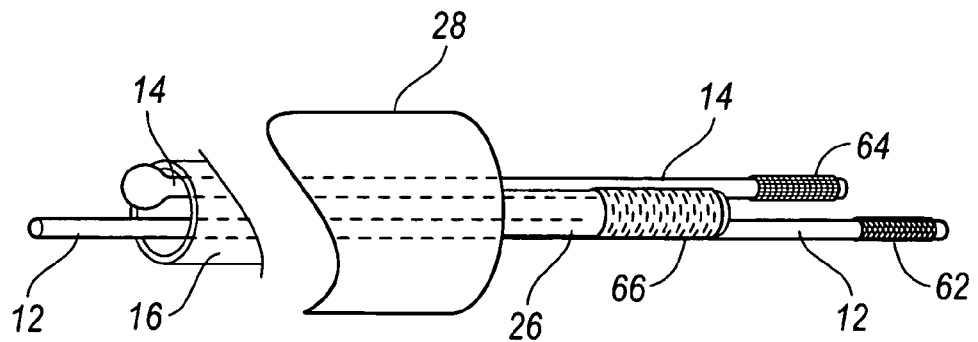
FIG. 14 is a side view of the proximal ends of the advancement device and wire guides according to the present invention.

Now referring to FIG. 14, the proximal end of the primary wire guide 12, the secondary wire guide 14, and the handle portion 26 are shown external the blood or other vessel. The handle portion 26, the primary wire guide 12, and the secondary wire guide 14, each have a distinctive mark, shown as mark 62, mark 64, and mark 66 respectively. Each mark 62, 64, 66 may be a different color allowing the clinician to easily distinguish between the handle portion 26, the first wire guide 12, and the secondary wire guide 14. For example, the mark 66 may be black, while mark 64 is green, and mark 62 is red. Alternatively, each mark may have a different tactile feature. For example, mark 62 may be knurled while mark 64 may have circularly aligned bumps, while mark 62 may have rows of bumps that are not circularly aligned. Accordingly, the clinician can easily distinguish in a tactile manner between each of the primary wire guide 12, the secondary wire guide 14, and the handle portion 26 without the need to refocus his attention to the proximal end of the instruments.

As a person skilled in the art will readily appreciate, the above description is meant as an illustration of implementation of the principles this invention. This description is not intended to limit the scope or application of this invention in that the invention is susceptible to modification, variation and change, without departing from the spirit of this invention, as defined in the following claims.

We claim:

1. A medical device for wire guide intraluminal deployment, the medical device comprising:
   a primary wire guide;
   an advancement device having a tubular portion with a distal opening and proximal opening, the primary wire guide extending through a hollow passage in the tubular portion, an edge region of the tubular portion forming the distal opening;
   a secondary wire guide extending through the hollow passage in the tubular portion, the secondary wire guide having a distal portion configured to engage the edge region of the tubular portion such that the secondary wire guide is advanced as the advancement device is translated to a region of interest, wherein the edge region includes a tab extending into the distal opening, the tab being positioned to engage the distal portion of the secondary wire guide, wherein the edge region that forms the distal opening is contiguous around the distal opening.

2. The medical device according to claim 1, wherein the distal portion of the secondary wire guide includes a tip of the secondary wire guide.

3. The medical device according to claim 2, wherein the tip is radiopaque.

4. The medical device according to claim 2, wherein the tip is rounded.

5. The medical device according to claim 1, wherein a handle portion of the advancement device extends proximally from the tubular portion.

6. The medical device according to claim 5, wherein the handle portion of the advancement device has a unique marker from the primary wire guide and the secondary wire guide.

7. The medical device according to claim 6, wherein the unique marker includes a color absent from the primary and secondary wire guide.

8. The medical device according to claim 7, wherein the unique marker is a tactile marker.

9. The medical device according to claim 1, wherein the tubular portion has a polygonal cross section.

10. The medical device according to claim 1, further comprising a guiding catheter, the guiding catheter having a lumen where the advancement device extends through the lumen of the guiding catheter.

11. The medical device according to claim 1, wherein the secondary wire guide includes a tip portion, the tip portion including an opening oriented to receive the tab extending from the edge region.

12. The medical device according to claim 1, wherein the tubular portion includes a side wall extending from the proximal opening to the distal opening.

* * * * *